United States Patent [19]

Kosower et al.

[11] Patent Number: 4,499,284
[45] Date of Patent: Feb. 12, 1985

[54] 1,5-DIAZABICYCLO[3.3.0.]OCTADIENEDIONES

[75] Inventors: Edward M. Kosower, Tel-Aviv, Israel; Barak Pazhenchevsky, Lawrence, Kans.; Eli Hershkowitz, Doar Na Hanegev, Israel

[73] Assignee: Tel Aviv University, Tel Aviv, Israel

[21] Appl. No.: 390,769

[22] Filed: Jun. 21, 1982

Related U.S. Application Data

[63] Continuation of Ser. No. 068,544, Aug. 27, 1979, abandoned, which is a continuation-in-part of Ser. No. 938,918, Sep. 5, 1978, abandoned.

[51] Int. Cl.³ .................................... C07D 231/54
[52] U.S. Cl. ..................................... 548/359; 424/7.1
[58] Field of Search .............................. 548/359, 369

[56] References Cited

PUBLICATIONS

Kosower et al. I, Proc. Natl. Acad. Sci., U.S.A., 1979, vol. 76, (7), (Jul.), pp. 3382–3386.
Kosower et al. II, J. Am. Chem. Soc., 1978, vol. 100, pp. 6516–6518.
Kosower et al. III, Biophysics Congress, Kyoto, Japan, Sep. 1978, Abstract & Charts, "Syn Bimane Bromides".

Primary Examiner—Henry R. Jiles
Assistant Examiner—Kurt G. Briscoe
Attorney, Agent, or Firm—Pennie & Edmonds

[57] ABSTRACT

Compounds of the formulas:

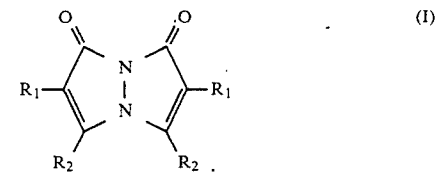

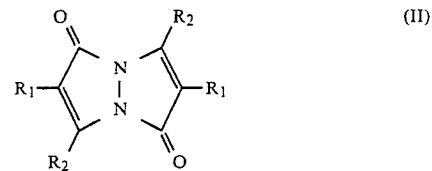

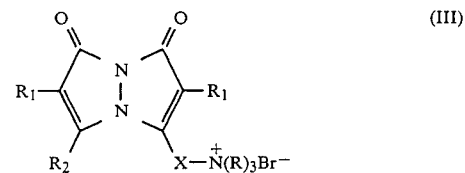

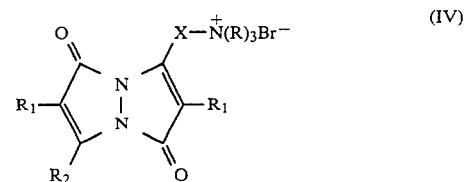

wherein R is independently branched or straight chain $C_1$–$C_4$ alkyl; $R_1$ is independently branched or straight chain $C_1$–$C_4$ alkyl, phenyl or halo; $R_2$ is independently branched or straight chain $C_1$–$C_{17}$ alkyl wherein at least one $R_2$ group has a bromo substituent on the carbon atom adjacent to the ring; and X is branched or straight chain $C_1$–$C_{17}$ alkylidene wherein the ring carbon and the quaternary nitrogen are attached to the same carbon atom are useful as chemical labeling agents which react readily with free sulfhydryl groups or primary amino groups to produce intensely fluorescent (when compounds I and III are used) and phosphorescent (when compounds II and IV are used) substances.

13 Claims, No Drawings

1,5-DIAZABICYCLO [3.3.0.]OCTADIENEDIONES

This is a continuation of application Ser. No. 068,544, filed Aug. 27, 1979, now abandoned, which is a continuation-in-part of Ser. No. 938,918, filed Sept. 5, 1978, also abandoned.

DESCRIPTION

1. Technical Field

This invention relates to novel synthetic compositions of matter and to processes for producing same. More particularly it relates to a new class of stable heterocyclic molecules which are useful as fluorescent and phosphorescent chemical (e.g., biochemical) labeling agents.

2. Background Art

A need has existed for improved chemical labeling agents, particularly biochemical labeling agents, in the form of stable, readily synthesizable molecules which undergo fluorecence or phosphorescene under appropriate and readily attainable and controllable conditions. While considerable research effort has been spent in the past on developing improved labeling agents, few if any have been produced which satisfy the foregoing requirements.

Accordingly, it is an object of the present invention to provide stable, readily synthesizable compounds useful for providing fluorescent or phosphorescent chemical (e.g., biochemical) labeling agents.

Another object is to provide a method for producing stable, readily synthesizable compounds useful for providing fluorescent or phosphorescent chemical (e.g., biochemical) labeling agents.

Another object is to provide fluorescent or phosphorescent chemical (e.g., biochemical) labeling agents derived from stable, readily synthesizable compounds, and to substances labeled with same.

Another object is to provide a method for producing fluorescent or phosphorescent chemical (e.g., biochemical) labeling agents from stable, readily synthesizable compounds, and substances labeled with same.

Yet another object is to provide methods for using substances labeled with the aforementioned fluorescent or phosphorescent labeling agents.

These and other objects of the invention as well as the advantages thereof can be had by reference to the following disclosure and claims.

DISCLOSURE OF THE INVENTION

The foregoing objects are achieved according to the present invention by the discovery of a new class of stable, isomeric heterocyclic organic molecules, namely, 1,5-diazabicyclo[3.3.0]octadienedione derivatives which have been found to be useful as fluorescent and phosphorescent labeling agents. More specifically, the present invention relates to compounds of the formulas:

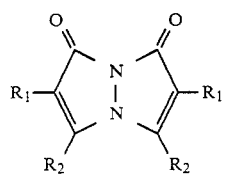

(I)

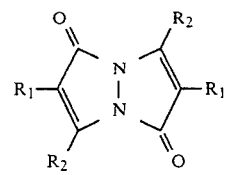

(II)

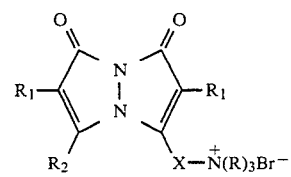

(III)

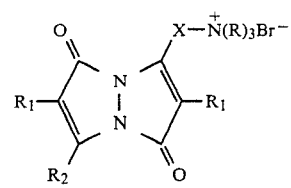

(IV)

wherein R is independently (i.e., the same or different) branched or straight chain $C_1$–$C_4$ alkyl; $R_1$ is independently branched or straight chain $C_1$–$C_4$ alkyl, phenyl or halo; $R_2$ is independently branched or straight chain $C_1$–$C_{17}$ alkyl, with the proviso that at least one $R_2$ group has a single bromo substituent on the carbon atom adjacent to the ring; and X is branched or straight chain $C_1$–$C_{17}$ alkylidene wherein the ring carbon and the quaternary nitrogen are attached to the same carbon atom.

Since the novel compounds of the instant invention are quite symmetrical, we have adopted the brief name "bimane" (bi, two and manus, hand) for the basic ring system and use a shorthand rotation to denote the various syn- and anti-isomers. Thus, when substitution on both sides of the molecule is identical (i.e., $R_1$=$R_1$; $R_2$=$R_2$) the notations syn-($R_2$, $R_1$)B and anti-($R_2$, $R_1$)B are used to denote compounds of formulas (I) and (II), respectively. If the substitution is not identical, the notations syn-($R_2$, $R_1$)($R_2'$, $R_1'$)B and anti-($R_2$, $R_1$)($R_2'$, $R_1'$)B are used. The shorthand notations employed for compounds of formula (III) and (IV) are thus syn-($R_2$,$R_1$)(Br−($R$)$_3$ N+X, $R_1'$)B and anti-($R_2$, $R_1$)(Br$^{31}$ ($R$)$_3$N+X, $R_1'$)B, respectively.

Preferred compounds within the scope of the present invention are the syn-bimanes of formulas (I) and (III) wherein $R_1$ is independently branched or straight –$C_4$ alkyl or halo (i.e., chloro, bromo, fluoro, iodo).

Particularly preferred compounds within the group described in the previous paragraph are those wherein both $R_1$ groups are identical. More particularly, preferred compounds within this group are those wherein the $R_1$ groups are methyl.

Especially preferred compounds within the group described in the previous paragraph are:

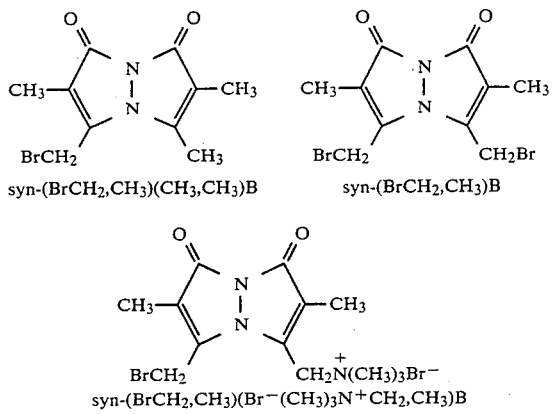

syn-(BrCH$_2$,CH$_3$)(CH$_3$,CH$_3$)B syn-(BrCH$_2$,CH$_3$)B syn-(BrCH$_2$,CH$_3$)(Br$^-$(CH$_3$)$_3$N$^+$CH$_2$,CH$_3$)B The bimane compounds of the present invention are extremely useful as chemical labeling agents which react readily with free sulfhydryl groups to afford intensely fluorescent substances when syn-bimanes are employed, and strongly phosphorescent substances when anti-bimanes are employed. The subject compounds also react with substances containing primary amino groups to afford fluorescent and phosphorescent materials, although the reaction conditions required are usually more rigorous.

Accordingly, a further aspect of the present invention relates to the use of the subject compounds as fluorescent and phosphorescent labeling agents and to substances labeled with same.

Labeling of free sulfhydryl group-containing substances with the compounds of formulas (I), (II), (III), and (IV) can be effected under a variety of reaction conditions, including but not limited to physiologically "normal" conditions in which labeling can be rapidly effected at pH 7.4 and 25° C. in aqueous media.

In view of the myriad of naturally occurring and synthetic substances containing free sulfhydryl groups, the range of substances capable of being labeled with the subject compounds is extensive. Representative examples of such substances include, but are not limited to, cells (e.g., red blood cells, lymphocytes, fibroblasts), proteins including immunoglobulins and enzymes, dyes, pigments and polymers.

In using the syn-bimane compounds for labeling normal human erythrocytes, it has been found that the non-ionic compounds of formula (I) penetrate cell membranes very readily while the ionic compounds of formula (III) do not. Specifically, it has been found that globin and membrane proteins are labeled by both mono- and bis-bromo syn-bimanes (I) after addition of the agents to intact red cells; neither membrane proteins nor globin is labeled when intact cells are treated with a mono-quaternary syn-bimane (III); and both membrane proteins and globin are labeled by (III) after lysis. Only the beta chains of the globin are labeled, the primary labeling site being beta$_{93}$ cysteine. Another labeled compound within the cell is glutathione.

A particularly useful application of the syn-bimanes of the instant invention is in the labeling of specific protein molecules, i.e., immunoglobulins, to afford fluorescent labeled antibodies. Antigenic materials containing free sulfhydryl groups can also be labeled with the subject compounds to afford fluorescent antigens.

In addition to the foregoing applications, it has been found that both syn- and anti-bimanes are effective in producing labeled polymers, dyes and pigments.

There are several important advantages to bimane labeled substances prepared according to the invention. For example, in addition to being intensely fluorescent or phosphorescent, the labeled materials are extremely stable to light, air and various routine chemical procedures. Moreover, convenient operating wavelengths can be used in measuring the extent of labeling. For instance, the fluorescence of substances labeled with syn-(BrCH$_2$, CH$_3$)(CH$_3$, CH$_3$)B, syn-(BrCH$_2$, CH$_3$)B and syn-(BrCH$_2$, CH$_3$)(Br$^-$(CH$_3$)$_3$N$^+$CH$_2$, CH$_3$)B can be determined at an excitation wavelength of 380 nm and an emission wavelength of 480 nm. Also, since the syn- and anti-bimanes of the instant invention are mutually compatible, it is possible to label a substance with both types of agent to afford a material having fluorescence as well as phosphorescence.

In a further aspect of the present invention, the following description relates to the synthesis of the novel bimanes of formulas (I), (II), (III), and (IV).

The bimanes of formulas (I) and (II), wherein R$_1$ is the same on the both rings, are prepared according to the following synthetic method and postulated reaction mechanism:

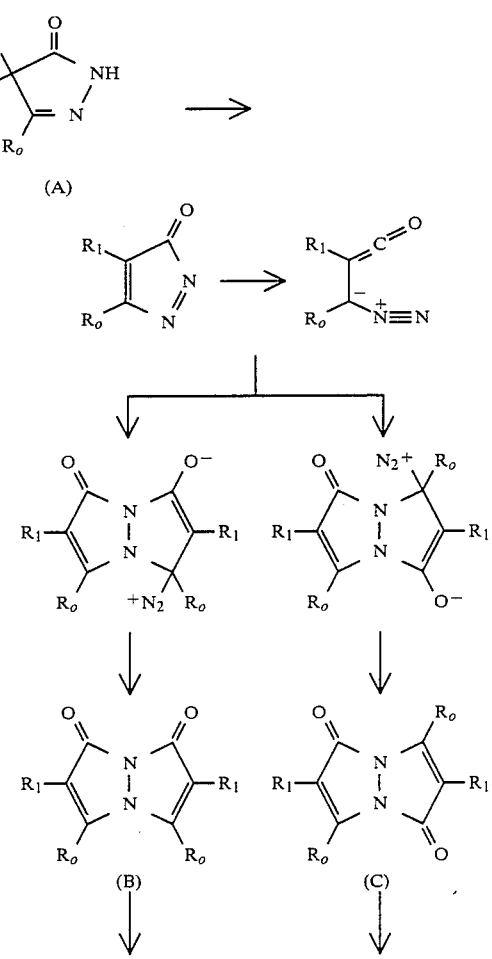

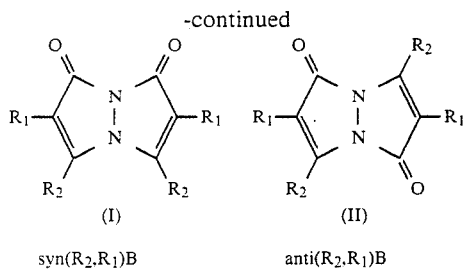

syn(R₂,R₁)B     anti(R₂,R₁)B wherein $R_o$ is a branched or straight chain $C_1$–$C_{17}$ alkyl group having at least one alpha hydrogen, Z is a suitable leaving group such as chloro or bromo and $R_1$ and $R_2$ are as previously described.

In the foregoing reaction sequence, an appropriately substituted 2-pyrazolin-5-one (A) is treated with a weak base to give an intermediate which reacts with its own decomposition product to produce the syn and anti isomers of formulas (B) and (C), respectively. Typically, the reaction is conducted in a suitable organic solvent such as methylene chloride, acetonitrile and the like. Suitable bases include alkali metal carbonates (e.g., $K_2CO_3$), bicarbonates (e.g., $NaHCO_3$), and hydroxides (e.g., KOH, NaOH) as well as ion-exchange resins in the hydroxide form.

The thus obtained mixed syn and anti isomers of formulas (B) and (C) respectively are converted to mono- or dibromo derivatives, preferably after separation, by reaction with stoichiometric amounts of bromine or other brominating agent. For example, syn-($BrCH_2$, $CH_3$)($CH_3$, $CH_3$)B can be produced by bromination of (B) wherein the $R_1$ and $R_o$ groups are methyl. Similarly, syn-($BrCH_2$, $CH_3$)B can be produced by bromination of syn-($BrCH_2$ $CH_3$)($CH_3$, $CH_3$)B. In a further embodiment, the foregoing mono- or dibromo derivatives can be converted to their chloro analogs by (a) displacement of $Br^-$ with $Cl^-$ using LiCl in DMSO (dimethylsulfoxide) with warming or (b) facile reaction of the corresponding alcohols (prepared from the bromo compounds by treatment with wet solium trifluoroacetate in acetonitrile) with thionyl chloride. Also, the corresponding mono- and bis-fluoro compounds can be made by reaction of the aforesaid alcohols with the reagent $Et_2NSF_3$. Furthermore, the alcohols can serve as intermediates in the formation of other derivatives, e.g., tosylates. Iodides may also be prepared via the reaction of alkali metal idoide (e.g., NaI) with the bromides.

When two different 2-pyroazolin-5-ones are employed in the preparation of compounds of formulas (I) and (II), mixed syn and anti isomers are produced as follows:

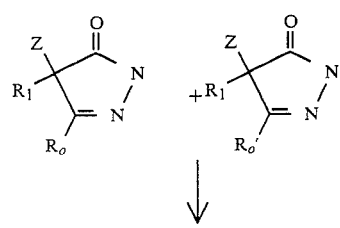

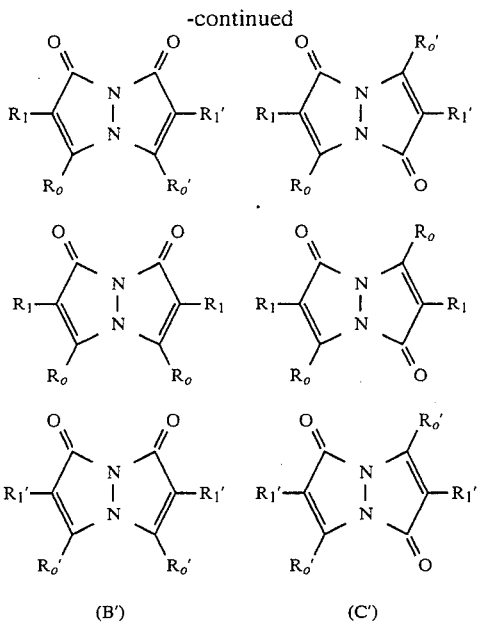

The mixed isomers of formulas (B′) and (C′) are converted to the mono and dibromo derivatives, after separation, by reaction with stoichiometric amounts of bromine.

The bimanes of formulas (III) and (IV) are respectively prepared by treating syn and anti compounds of the type ($R_2$, $R_1$)B or ($R_2$, $R_1$)($R_2'$, $R_1'$), wherein the $R_2$ and $R_1$ groups contain a bromo substituent on the carbon atom adjacent the ring, with a $C_1$–$C_4$ alkyl tertiary amine. Reaction is typically carried out in an organic solvent at room temperature.

DESCRIPTION OF PREFERRED EMBODIMENTS

The following examples are provided for the purpose of illustrating, without limitation, the present invention and the advantages thereof. In the examples, the pyrazolinone starting materials are available by synthetic procedures and methods well known in the art. Structures of the products can be confirmed using the methods and procedures described in JACS, 100, 6516-8 (1978) and JACS, 101, 1620-1 (1979).

Preparation of 3,4-dimethyl-4-chloro-2-pyrazolin-5-one

A quantity (137.8 g) of 3,4-dimethyl-2-pyrazolin-5-one is charged, together with 1.2 liters of 1,2-dichloroethane, into a 3-neck, 2-liter flask equipped with a gas inlet, reflux condenser, and a gas outlet which is connected to a $Cl_2$ trap (bisulfite solution). Chlorine is introduced at a rate such that the solution gently boils and until the solid has dissolved and the solution acquires a green-yellow color. The reaction mixture is then cooled to room temperature and stirred for one-half hour. Thereafter after, air is bubbled through the system for 10 minutes to removed dissolved chlorine and the solution is filtered. Evaporation of the filtrate affords a white oil which is taken up in 300 ml of hot solvent (1:1 benzene:petroleum ether). Upon cooling the solution, 110.7 g of crystalline 3,4-dimethyl-4-chloro-2-pyrazolin-5-one precipitates and is collected by filtration. Evaporation of the filtrate and further cooling yields an additional 21 g of product, m.p. 56° C.

EXAMPLE I

Preparation of Syn- And Anti- (BrCH$_2$, CH$_3$)B and (BrCH$_2$, CH$_3$)(CH$_3$, CH$_3$)B A quantity (70 g, 0.48 mole) of 3,4-dimethyl-4-chloro-2-pyrazolin-5-one, produced according to the foregoing recitation, is dissolved in 500 ml of methylene chloride and the resulting solution is added over a period of 1-2 minutes to a cooled (ice bath), vigorously stirred mixture of 150 g of K$_2$CO$_3$ · ½ H$_2$O, 50 g of anhydrous K$_2$CO$_3$ and 250 ml of methylene chloride. After one hour, the ice bath is removed and stirring is continued at room temperature for 18 hours. During this period, the crystalline K$_2$CO$_3$ · ½ H$_2$O becomes suspended in finely divided form. Celite (powdered diatomaceous earth; 50 g) is added and the mixture is filtered with suction through a celite layer approximately 5 mm thick. Evaporation of the yellow filtrate yields a solid yellow residue which is dissolved in the smallest possible volume (ca. 150 ml) of boiling acetonitrile. Upon cooling to room temperature, 27.5 g of syn-(CH$_3$, CH$_3$)B is deposited. Further cooling yields more precipitate which contains a small amount of anti-(CH$_3$, CH$_3$)B. Recrystallization of this fraction from acetonitrile yields 2.5 g of syn-(CH$_3$, CH$_3$)B, m.p. 211°–212° C. The filtrate is evaporated and the residue taken up in methylene chloride and partitioned by column chromatography (150 g activity grade neutral alumina) using 2 or 3 elutions with methylene chloride. In order of elution, 2.1 g of anti-(CH$_3$, CH$_3$)B and 1.6 g of syn-(CH$_3$, CH$_3$)B are obtained.

A quantity (1.92 g; 0.005 mole) of syn-(CH$_3$, CH$_3$)B is dissolved in 50 ml of methylene chloride and thereafter 2.56 g (0.021 mole) of bromine in 25 ml of methylene chloride is added dropwise to the bimane solution over a period of 1 hour. When approximately ½ of the bromine solution has been added, a white precipitate appears which redissolves toward the end of the addition. Approximately ½ the reaction solution is then evaporated leaving a red oil which is dissolved in hot ethyl acetate. On cooling to room temperature, the product precipitates to afford 2.56 g of syn-(BrCH$_2$, CH$_3$)B, m.p. 176°–178° C.

The use of 1.28 g (0.010 mole) of bromine in the foregoing bromination procedure produces syn-(BrCH$_2$, CH$_3$)(CH$_3$, CH$_3$)B.

Moreover, when syn-(CH$_3$, CH$_3$)B is replaced with anti-(CH$_3$, CH$_3$)B in the foregoing procedure, anti-(BrCH$_2$, CH$_3$)B or anti-(BrCH$_2$, CH$_3$)(CH$_3$, CH$_3$)B can be obtained, depending on the amount of bromine employed.

EXAMPLE II

Using the appropriate 2-pyrazoline-5-ones in the procedure of Example I, the following representative monobromo and dibromo syn and anti-bimanes are obtained:

| Monobromobimanes | | | |
|---|---|---|---|
| R$_2$ | R$_1$ | R$_2'$ | R$_1'$ |
| BrCH$_2$— | Cl— | CH$_3$— | Cl— |
| BrCH$_2$— | C$_4$H$_9$— | CH$_3$— | C$_4$H$_9$— |
| BrCH$_2$— | C$_6$H$_5$— | CH$_3$— | C$_6$H$_5$— |
| BrCH$_2$— | C$_6$H$_5$— | CH$_3$— | Cl |
| BrCH$_2$— | CH$_3$— | CH$_3$— | Cl— |
| BrCH$_2$— | Cl— | CH$_3$— | CH$_3$— |
| BrCH(CH$_2$)$_2$CH$_3$ | CH$_3$— | CH$_3$(CH$_2$)$_3$— | CH$_3$— |
| BrCH(CH$_2$)$_6$CH$_3$ | CH$_3$— | CH$_3$(CH$_2$)$_7$— | CH$_3$— |
| BrCH(CH$_2$)$_{13}$CH$_3$ | CH$_3$— | CH$_3$(CH$_2$)$_{14}$— | CH$_3$— |

| Dibromobimanes | | | |
|---|---|---|---|
| | | Given only when different from R$_1$ and R$_2$ | |
| R$_2$ | R$_1$ | R$_2'$ | R$_1'$ |
| BrCH$_2$— | Cl— | | |
| BrCH$_2$— | C$_4$H$_9$— | | |
| BrCH$_2$— | C$_6$H$_5$— | | |
| BrCH(CH$_2$)$_2$CH$_3$ | CH$_3$— | | |
| BrCH(CH$_2$)$_6$CH$_3$ | CH$_3$— | BrCH$_2$— | |
| BrCH(CH$_2$)$_{13}$CH$_3$ | CH$_3$— | BrCH$_2$— | |
| BrCH$_2$— | CH$_3$— | | Cl— |
| BrCH$_2$ | C$_6$H$_5$— | | Cl— |

EXAMPLE III

Preparation of Syn-(BrCH$_2$, CH$_3$)(Br$^-$(CH$_3$)$_3$N$^+$CH$_2$, CH$_3$)B Ten grams of syn-(BrCH$_2$, CH$_3$)B prepared according to Example I, is dissolved in 150 ml of chloroform and 8.1 ml of 25% trimethylamine in methanol is then added to the solution. After stirring the reaction mixture at room temperature for 2 hours, the product is collected by filtration and dried under vacuum to afford 11 g of syn-(BrCH$_2$, CH$_3$)(Br$^-$(CH$_3$)$_3$N$^+$CH$_2$, CH$_3$)B.

The foregoing procedure can be used for the preparation of all compounds of formulas III and IV when appropriate reactants are employed.

EXAMPLE IV

The following example illustrates the use of a representative bimane of the instant invention as a fluorescent labeling agent.

A quantity (25 mg) of gamma-immunoglobulin (IgG) is dissolved in 5 ml of a solution containing 8 M urea, 0.1% ethylenediamine tetraacetic acid and 0.2 M tris buffer at a pH of 7.5. To this solution is added a solution of syn-(Br$_2$CH$_2$,CH$_3$)B in 250 μof DMSO dropwise over a period of several minutes. After the addition is complete, The reaction mixture is stirred for 30 minutes, diluted to 20 ml with water and then dialyzed against 0.1 M tris buffer at pH 7.5 for 24 hours whereupon a fluorescent solution is obtained which can be used per se.

A greater incorporation of labeling agent can be achieved by pretreating the IgG with 1–10 molar equivalents of mercaptoethanol for one hour and then dialyzing to remove excess mercaptoethanol prior to adding the labeling agent.

EXAMPLE V

The following example illustrates additional labeling of immunoglobulins with a representative compound of the instant invention.

A quantity (0.5 ml) of goat-antihuman serum is mixed with 0.5 ml of 0.5 M sodium carbonate buffer (pH 9) and 20 μl of a solution of syn-(BrCH$_2$, CH$_3$)B in ethanol. After five minutes at room temperature, the solution is applied to a 1×7 cm column of Sephadex G 25 and eluted with phosphate buffered saline (PBS). A fluorescent band of labeled immunoglobulins eluting in the void volume is collected; a larger band of unreacted syn-(BrCH$_2$, CH$_3$)B, emerging more slowly, is discarded.

The collected labeled immunoglobulin fraction obtained above can be used directly in immunoassay.

The foregoing examples are provided for illustrative purposes only. It is understood than changes and variations can be made therein without departing from the scope of the present invention which is defined in the following claims.

We claim:

1. A 1,5-diazabicyclo[3.3.0]octadienedione having a formula selected from the group consisting of:

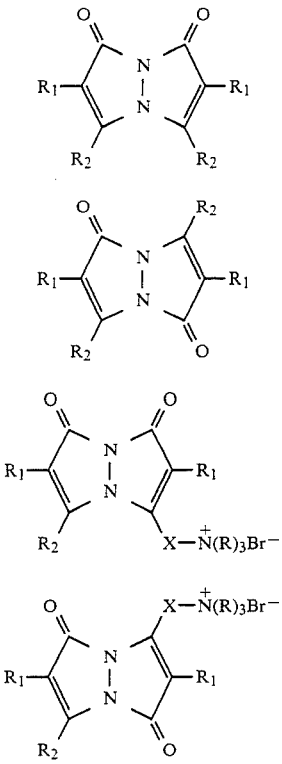

wherein R is independently branched or straight chain $C_1-C_4$ alkyl; $R_1$ is independently branched or straight chain $C_1-C_4$ alkyl, phenyl or halo; $R_2$ is independently branched or straight chain $C_1-C_{17}$ alkyl wherein at least one $R_2$ group has a bromo substituent on the carbon atom adjacent to the ring; and X is branched or straight chain $C_1-C_{17}$ alkylidene wherein the ring carbon and the quarternary nitrogen are attached to the same carbon atom.

2. A compound according to claim 1 having the formula (I) wherein $R_1$ is independently branched or straight chain $C_1-C_4$ alkyl or halo.

3. A compound according to claim 2 wherein both $R_1$ groups are identical.

4. A compound according to claim 3 wherein both $R_1$ groups are methyl.

5. The compound according to claim 4 having the formula:

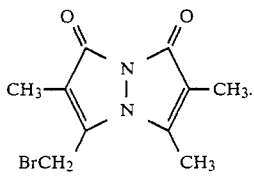

6. The compound according to claim 4 having the formula:

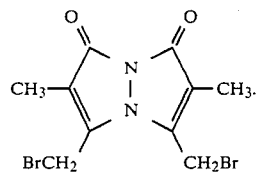

7. A compound according to claim 1 having the formula (III) wherein $R_1$ is independently branched or straight chain $C_1-C_4$ alkyl or halo.

8. A compound according to claim 7 wherein both $R_1$ groups are identical.

9. A compound according to claim 8 wherein both $R_1$ groups are methyl.

10. The compound according to claim 9 having the formula:

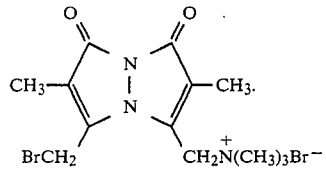

11. A process for preparing a compound having a formula selected from the group consisting of:

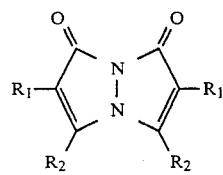

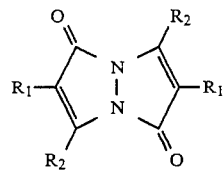

wherein $R_1$ is independently branched or straight chain $C_1-C_4$ alkyl, phenyl or halo and $R_2$ is independently branched or straight chain $C_1-C_{17}$ alkyl wherein at least one $R_2$ group has a bromo substituent on the carbon atom adjacent to the ring, said process comprising:

(a) reacting a base with a pyrazolinone of the formula:

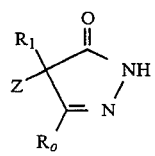

wherein $R_o$ is branched or straight chain $C_1-C_{17}$ alkyl, having at least one alpha hydrogen, and Z is a chloro or bromo leaving group; and (b) reacting the product of step (a) with a stoichiometric amount of bromine.

12. A process according to claim 11 wherein the base used in step (a) is selected from the group consisting of alkali metal carbonates, alkali metal bicarbonates, alkali metal hydroxides and ion exchange resins in the hydroxide form.

13. A process for preparing a compound having a formula selected from the group consisting of:

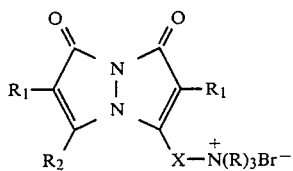

III

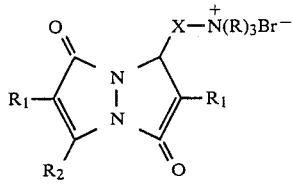

IV wherein R is independently branched or straight chain $C_1$-$C_4$ alkyl; $R_1$ is independently branched or straight chain $C_1$-$C_4$ alkyl, phenyl or halo; $R_2$ is independently branched or straight chain $C_1$-$C_{17}$ alkyl having a bromo substituent on the carbon atom adjacent to the ring; and X is branched or straight chain $C_1$-$C_{17}$ alkylidene wherein the ring carbon and the quaternary nitrogen are attached to the same carbon atom, said process comprising:

(a) reacting a base with a pyrazolinone of the formula:

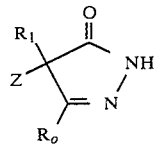

wherein $R_o$ is branched or straight chain $C_1$-$C_{17}$ alkyl, having at least one alpha hydrogen, and Z is a chloro or bromo leaving group;

(b) reacting the product of step (a) with a stoichiometric amount of bromine to produce a compound selected from the group represented by the formulas:

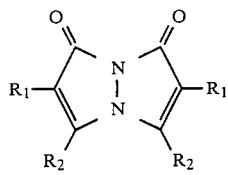

I

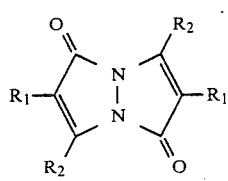

II wherein the compounds of formulas (I) and (II) are used to produce respectively the compounds (III) and (IV); and (c) reacting the product of step (b) with a stoichiometric amount of a $C_1$-$C_4$ alkyl tertiary amine of the formula $N(R)_3$.

* * * * *